(12) United States Patent
Iwase et al.

(10) Patent No.: US 9,289,463 B2
(45) Date of Patent: Mar. 22, 2016

(54) OCTREOTIDE-MODIFIED NANOMEDICINE FOR CANCER TREATMENT OR CANCER PALLIATIVE CARE

(75) Inventors: Yuko Iwase, Sagamihara (JP); Yoshie Maitani, Tokyo (JP)

(73) Assignee: NANOSION CO., LTD., Kashiwa-shi, Chiba (JP)

( * ) Notice: Subject to any disclaimer, the term of this patent is extended or adjusted under 35 U.S.C. 154(b) by 0 days.

(21) Appl. No.: 13/823,821

(22) PCT Filed: Feb. 23, 2011

(86) PCT No.: PCT/JP2011/053890
§ 371 (c)(1),
(2), (4) Date: Mar. 15, 2013

(87) PCT Pub. No.: WO2012/035794
PCT Pub. Date: Mar. 22, 2012

(65) Prior Publication Data
US 2013/0171243 A1    Jul. 4, 2013

(30) Foreign Application Priority Data
Sep. 17, 2010 (JP) ................................. 2010-208744

(51) Int. Cl.
*A61K 38/08* (2006.01)
*A61K 31/4745* (2006.01)
*A61K 9/127* (2006.01)

(52) U.S. Cl.
CPC ............... *A61K 38/08* (2013.01); *A61K 9/1271* (2013.01); *A61K 31/4745* (2013.01)

(58) Field of Classification Search
None
See application file for complete search history.

(56) References Cited

U.S. PATENT DOCUMENTS

2004/0219205 A1 * 11/2004 Kan et al. .................... 424/450

FOREIGN PATENT DOCUMENTS

| EP | 1 118 336 A2 | 7/2001 |
| JP | 2002-47298 A | 2/2002 |
| WO | WO -03030864 | * 4/2003 |

OTHER PUBLICATIONS

Erten C, Regulation of growth factors in hormone- and drug-resistant prostate cancer cells by synergistic combination of docetaxel and octreotide, BJUI, 2009, 104, 107-114.*
Hattori Y, Novel irinotecan loaded liposome using phytic acid with high therapeutic efficacy for colon tumors, JCR, 2009, 30-37.*
Sun M, Octreotide modification enhances the delivery and targeting of doxorubicin loaded liposomes to somatostatin receptors expressing tumor in vitro and in vivo, Nanotechnology, 21, 2010, 475101.*
Chang, C. et al., "Liposome encapsulation reduces cantharidin toxicity," Food and Chemical Toxicology, vol. 46, No. 9, 2008, pp. 3116-3121.
Chen, C. et al., "Evaluation of Multi-Target and Single-Target Liposomal Drugs for the Treatment of Gastric Cancer", Biosci., Biotechnol., Biochem, vol. 72, No. 6, 2008, pp. 1586-1594.
International search report issued in PCT/JP2011/053890 mailed May 10, 2011.
Iwase, Y. et al., Abstract of 130th Annual Meeting of Pharmaceutical Society of Japan, Mar. 5, 2010, 28CE-pm03.
Ohno, R. et al., "An Early Phase II Study of CPT-11: A New Derivative of Camptothecin, for the Treatment of Leukemia and Lymphoma", Journal of Clinical Oncology, vol. 8, No. 11, 1990, pp. 1907-1912.
International Preliminary Report on Patentability and English translation of Written Opinion issued Apr. 25, 2013, in PCT International Application No. PCT/JP2011/053890.

* cited by examiner

*Primary Examiner* — Brian Gulledge
*Assistant Examiner* — Celeste A Roney
(74) *Attorney, Agent, or Firm* — Birch, Stewart, Kolasch & Birch, LLP

(57) ABSTRACT

The present invention relates to a medical composition for treatment, palliative care or prevention of cancer, such as medullary thyroid carcinoma. Specifically, the invention relates to a medical composition for treatment, palliative care or prevention of medullary thyroid carcinoma, which comprises liposomes modified with octreotide.

5 Claims, 7 Drawing Sheets

OCTREOTIDE-MODIFIED NANOMEDICINE FOR CANCER TREATMENT OR CANCER PALLIATIVE CARE

TECHNICAL FIELD

The present invention relates to a medical composition for treatment, prevention of cancer, such as medullary thyroid carcinoma or palliative care. Specifically, the invention relates to a medical composition for treatment, palliative care or prevention of cancer, such as medullary thyroid carcinoma, which comprises liposomes modified with octreotide.

BACKGROUND ART

Medullary thyroid carcinoma (MTC) is a rare cancer resulting from canceration of C cells of the thyroid gland. MTC is treated by surgical excision, but this has a problem that it caused reduced Quality of Life (QOL) for patients.

The irinotecan (CPT-11) which is a camptothecin derivative has the potential for efficacy against MTC, but CPT-11 has a short half-life and produces serious side-effects, and therefore its use has been limited (NPL 1).

When an anticancer agent is encapsulated in liposomes, it is known that accumulation of the drug in the tumor increases by passive targeting, allowing side-effects to be reduced. Further, modification of the liposomes with a ligand can also enhance the therapeutic effect of the liposomes. For example, treatment of breast cancer and stomach cancer has been attempted using anticancer agents such as cantharidin or dihydrotanshinone encapsulated in liposomes modified with octreotide (Oct) which is a high-affinity ligand for somatostatin receptor (SSTR) (NPL 2 and 3).

The present inventors have previously prepared Oct-modified CPT-11-encapsulating liposomes, and have reported that they exhibit in vitro cytotoxicity against MTC-derived cell lines that express SSTR (NPL 4). However, no effective in vivo method has been established for treatment of MTC.

PRIOR ART DOCUMENTS

Non-Patent Literature

[NPL 1] Ohno, R. et al., J. Clin. Oncol., 8:1907-1912 (1990)
[NPL 2] Chang, C. C. et al., Food Chem. Toxicol., 46:3116-3121 (2008)
[NPL 3] Chen, C. H. et al., Biosci. Biotechnol. Biochem., 72:1586-1594 (2008)
[NPL 4] Iwase, Y. et al., Proceedings of the 130th Meeting of The Pharmaceutical Society of Japan, 28CE-pm03 (2010).

SUMMARY OF INVENTION

Problems to be Solved by the Invention

An object of the present invention is providing a medical composition for treatment, palliative care or prevention of cancer, such as medullary thyroid carcinoma.

Means of Solving the Problems

The invention relates to the following.

[1] A medical composition for treatment, palliative care or prevention of cancer, which comprises liposomes modified with octreotide.

[2] The medical composition according to [1], wherein the concentration of octreotide in the liposomes is greater than 0.8 mol %.

[3] The medical composition according to [1] or [2], wherein the liposomes are further modified with poly(ethylene glycol).

[4] The medical composition according to any one of [1] to [3], wherein the % ILS representing the Increase of Life-Span, with physiological saline as the control, is 100 or greater.

[5] The medical composition according to any one of [1] to [4] above, wherein irinotecan is encapsulated in the liposomes.

[6] The medical composition according to [5], wherein the irinotecan dosage is no greater than 20 mg/kg body weight.

[7] The medical composition according to any one of [1] to [6], wherein the cancer is medullary thyroid carcinoma.

Effects of the Invention

According to the invention there is provided a medical composition for treatment, palliative care or prevention of cancer such as medullary thyroid carcinoma, which comprises liposomes modified with octreotide.

DESCRIPTION OF EMBODIMENTS

Figure 1:
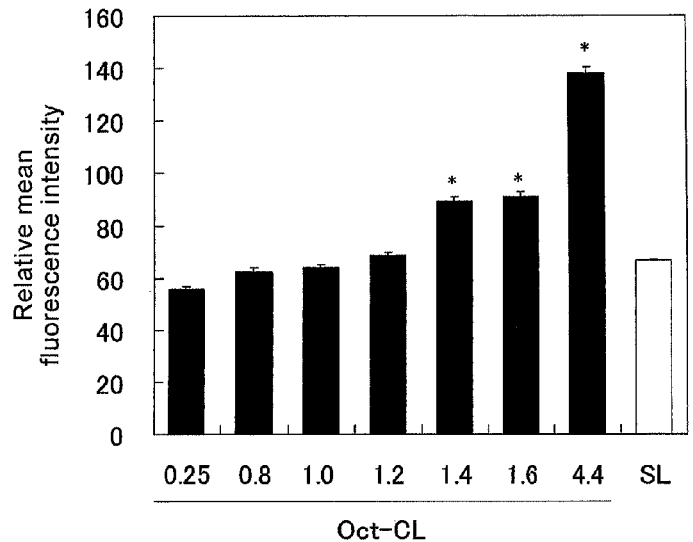
FIG. 1 provides the effect of Oct concentration with respect to intracellular uptake. The values are mean±SD (n=3). The "*" symbols indicate a significant difference (p<0.05) compared to SL.

The present invention provides a medical composition for treatment, palliative care or prevention of cancer, such as medullary thyroid carcinoma.

The term "medullary thyroid carcinoma" (also referred to as "MTC" throughout the present specification) as used herein refers to malignant endocrine tumor arising from calcitonin-secreting follicular cells (C cells) of the thyroid gland. MTC constitutes approximately 3-5% of thyroid cancers. A portion of 75% of MTC is sporadic, with the remaining 25% being familial (multiple endocrine neoplasia IIA (MEN2A), multiple endocrine neoplasia IIB (MEN2B) and familial medullary thyroid carcinoma (FMTC)). It is known that somatostatin receptors are expressed on MTC.

The term "somatostatin receptor" (also referred to as "'SSTR" throughout the present specification), as used herein, refers to a receptor whose ligand is the growth hormone secretion inhibiting factor, i.e., somatostatin. SSTR is a seven trans-membrane G protein-coupled receptor, which is overexpressed in MTC as well as in neuroendocrine tumor, gastroenteropancreatic tumor, pituitary tumor, carcinoid tumor and the like (see below). When a somatostatin analog binds to SSTR, a signal is transferred via phosphorylation of PI3K, Akt, TSC2, mTOR and p70S6K, and the cell cycle is interrupted (PI3K/Akt/TSC2/mTOR/p70S6K signal cascade) (Grozinsky-Glasberg, S. et al., Endocr. Relat. Cancer, 15:701-720 (2008); Theodoropoulou, M. et al., Cancer Res., 66:1576-1582 (2006)).

The somatostatin receptor has five subtypes (sst1-5), and octreotide has high affinity for the somatostatin receptor subtypes sst2, sst3 and sst5 (Patel, Y. C., Frontiers in Neuroendocrinology, 20:157-198 (1999)). Neural crest cells that migrate as the neural tube closure during embryogenesis exhibit immunoreactivity against somatostatin, and characteristics derived from adrenal (catecholamine positive). This event occurs only during early development of neural crest cells (Maxwell, G. D. et al., Developmental Biology, 108:203-209 (1985); Garcia-Arraras, J. E. et al., Cell and Tissue Research, 295:33-41 (1999)), and almost disappear after birth. Cells that have lost these somatostatin receptors express somatostatin receptors again during development of cancer. The following cancers are known to have selectivity for subtypes sst2, sst3 and sst5: medullary thyroid carcinoma (C cells); pituitary inactive adenoma; pituitary growth hormone adenoma; renal cell carcinoma, gastroenteropancreatic tumor (chromaffin cells); pheochromocytoma; neuroblastoma/medulloblastoma/meningioma; lymphoma; paraganglioma ((Reubi, J. C. et al., European Journal of Nuclear Medicine, 28:836-846 (2001)); breast cancer (estrogen receptor-bearing cells) (Reubi, J. C. et al., Ibid.); Orlando, C. et al., Endocrine-Related Cancer, 11:323-332 (2004)); small-cell lung cancer (Reubi, J. C. et al. (Ibid.); Papotti, M. et al., Virchows Archiv, 439:787-797 (2001)); hepatocarcinoma (Reubi, J. C. et al. (Ibid.); Blaker, M. et al., Journal of Hepatology, 41:112-118 (2004)); intraocular uveal melanoma (Filali, M. K. E. et al., Graefes Archive for Clinical and Experimental Ophthalmology, 246:1585-1592 (2008)); metastatic sarcoma (Friedberg, J. W. et al., Cancer, 86:1621-1627 (1999)); melanoma (Lum, S. S. et al., World Journal of Surgery, 25:407-412 (2001)); endothelial cells surrounding cancer tissue (Denzler, B. et al., Cancer, 85:188-198 (1999)); and acute myelocytic leukemia (locomotive acute myelocytic leukemia cells) (Oomen, S. P. M. A. et al., Leukemia, 15:621-627 (2001)). The invention is therefore effective for any such cancer that expresses somatostatin receptors.

The invention provides a medical composition for treatment, palliative care or prevention of cancer such as medullary thyroid carcinoma, which comprises liposomes modified with octreotide. The invention further provides a method for treatment, palliative care or prevention of cancer such as MTC, which includes a step of administering a composition of the invention. The medical composition of the invention generally has a size larger than 1 nanometer. Such a medical composition will also be referred to as "nanomedicine" throughout the present specification. Also, a size of greater than 1 nanometer will be referred to as "nanosize" throughout the present specification.

According to the invention, an SSTR-binding substance is used as the ligand. The SSTR-binding substance is preferably octreotide. "Octreotide" (also referred to herein as "Oct" in the present specification) is a cyclic peptide comprising 8 amino acids, retaining the sequence of the four amino acids (Phe-Trp-Lys-Thr) which constitute the essential portion exhibiting the biological activity of somatostatin, and it is a somatostatin analog with high affinity for SSTR and an increased blood plasma half-life. The SSTR-binding substance is not limited to octreotide, and it may be any substance that has the ability to bind to SSTR and exhibits toxicity against cancer cells such as MTCs when used in the medical composition of the invention may be used.

The term "liposome", as used herein, refers to a vesicle obtained using a phospholipid. Any desired phospholipid may be used for the invention. Examples of phospholipids include, but are not limited to, phosphatidylcholine, phosphatidylethanolamine, phosphatidylinositol and sphingomyelin. Distearoylphosphatidylcholine (DSPC) and distearoylphosphatidylethanolamine (DSPE) are preferred for use. Further, other lipids such as cholesterol (Chol) may also be added.

According to one embodiment, the liposomes of the invention may be further modified with poly(ethylene glycol). The term "poly(ethylene glycol)" (also referred to as "PEG"), as used herein, refers to a polymerized polyether of ethylene glycol. PEG of any desired molecular weight may be used for the invention, but the molecular weight of the PEG is preferably 500 or greater, more preferably 1000 or greater and even more preferably 1500 or greater, and preferably no greater than 6000, more preferably no greater than 5000 and even more preferably no greater than 4000. For example, PEG has an average molecular weight of 3400.

The proportion of Oct with respect to the liposomes, i.e. the Oct concentration of the liposomes, is greater than 0.8 mol %, for example, and preferably 1.0 mol % or greater, more preferably 1.2 mol % or greater, even more preferably 1.4 mol % or greater and yet more preferably 1.6 mol % or greater. The present inventors have found that a higher Oct concentration is effective for cytotoxicity against MTC cells. Therefore, the octreotide concentration of the liposomes is preferably higher, but is no greater than 10 mol %, for example, and preferably no greater than 8 mol %, more preferably no greater than 6 mol % and even more preferably no greater than 5 mol %. The Oct concentration of liposomes used in previous reports relating to Oct-modified liposomes is approximately 0.5 mol % (NPL 2, 3), but according to the invention it is preferred to use a higher concentration of Oct.

Liposomes containing Oct and PEG can be obtained according to the method described in Hattori, Y. et al., J. Control. Release, 136:30-37 (2009), for example, by mixing DSPC and Chol, adding phytic acid (IP-6) and agitating to prepare liposomes, and then adding an Oct, PEG, DSPE conjugate (Oct-PEG-DSPE) thereto (modification after preparation). Alternatively, liposomes containing Oct and PEG may be prepared according to the method described in Hattori, Y. et al., by mixing DSPE, Chol and Oct-PEG-DSPE, adding phytic acid (IP-6) and agitating the mixture.

Modification with Oct is not limited to the method described above, and any method known in the technical field may be employed so long as Oct is present in the liposomes in a form bonded to SSTR.

Further, when the liposomes are prepared by the method described above, the amount of PEG in each liposome will be determined by the amount of Oct-PEG-DSPE in which Oct is bonded, but liposomes without PEG may be prepared, or the amount of PEG may be increased or decreased as desired. Methods for this are well known in the technical field.

When the drug is intravascularly administered, since the majority of blood capillaries in the body only allow molecules smaller than nanosize to pass, a nanomedicine will not be able to easily pass through blood vessels surrounding normal cells and reach the cells. Therefore, an intravascularly administered nanomedicine maintains a high concentration in the blood vessels (Igarashi, E., Toxicol Appl Pharmacol, 229: 121-34 (2008)). On the other hand, since in the marginal of cancer cells, angiogenesis is active and proliferation potency is high, even nanosize substances can easily pass through the blood vessels. An intravascular nanomedicine, therefore, has selectivity for cancer tissue. The target nanomedicine uses a peptide (Oct), which has high affinity for somatostatin receptors strongly expressed in particular abundance in cells during tumorigenesis, as the cancer cell target, and the tissue selectivity provided by the nanosize allows it to selectively reach cancer tissue, the cancer cell selectivity resulting in uptake by cancer cells, whereupon interaction with the cancer cells allows for longer retention in the cancer tissue so that an advantage is provided for efficacy and safety compared to non-targeted nanomedicines, thus promising to lead to improved QOL for patients.

According to one embodiment, a drug may be encapsulated in the liposomes of the invention. A drug can be encapsulated in the aforementioned liposomes by adding the drug to the liposomes during their preparation. The drug:liposome weight ratio is determined as appropriate, and for example, it may be at least 0.1:1, preferably at least 0.2:1 and more preferably at least 0.4:1, and no greater than 1:1, preferably no greater than 0.8:1 and even more preferably no greater than 0.6:1.

Examples of drugs that may be used include any anticancer agents such as irinotecan and doxorubicin. Preferably, a drug encapsulated in the liposomes of the invention is an anticancer agent that acts on cancer such as MTC, and more preferably irinotecan. The drug "irinotecan" (also referred to herein as "CPT-11") is a water-soluble derivative of camptothecin, and it is converted to the active form SN-38 by carboxyesterase, and inhibits topoisomerase. Administration of CPT-11 is known to produce side-effects such as diarrhea, enteritis, myelosuppression, nausea, vomiting, melena, intestinal obstruction and interstitial pneumonitis. The drug dosage, in the case of CPT-11 for example, may be less than 30 mg/kg body weight, preferably no greater than 25 mg/kg body weight, more preferably no greater than 20 mg/kg body weight and even more preferably no greater than 15 mg/kg body weight, and at least 1 mg/kg body weight, preferably at least 2 mg/kg body weight, more preferably at least 5 mg/kg body weight and most preferably about 10 mg/kg body weight. According to the invention, the dosage of a drug such as CPT-11 can be reduced, thereby allowing the various side-effects conventionally associated with high doses (30 mg/kg body weight) to be alleviated.

Vomiting is an occurrence following anticancer agent therapy or surgery. This is a factor causing reduced QOL for patients. Vomiting is suppressed by using drugs such as antisecretory agents and antiemetic drugs, either alone or in combination. Oct can rapidly reduce gastrointestinal secretion, and plays a particularly important role for patients with advanced intestinal obstruction for which the antispastic drug hyoscine/butyl bromide is ineffective. Oct is used as a therapeutic agent for palliative care, and can be used as concurrent treatment with other palliative care drugs such as morphine, hyoscine/butyl bromide and haloperidol (Ripamonti, C. I. et al., European Journal of Cancer, 44:1105-1115 (2008)). Currently, treatment with Oct used as a prescription drug offers cellular selectivity, but because it is not nanosized, it can provide no selectivity for tissue surrounding pain regions. However, by formulating an Oct-modified nanomedicine encapsulating a drug in combination with Oct, it is possible to provide a more effective therapeutic agent for palliative care, since it selectively accumulates in tissue surrounding regions of pain, and accumulates in both tissue and cells surrounding regions of pain due to the cellular selectivity of Oct.

Administration of the medical composition of the invention may be either systemic administration or local administration. The route of administration may be any desired route such as intravenous, subcutaneous, intraperitoneal, intramuscular or intranasal. The medical composition of the invention may further contain desired components used in the field of pharmaceuticals, such as excipients, diluents or stabilizers.

The medical composition of the invention may be evaluated in vitro based on an index such as cytotoxicity for a cancer-derived cell line such as MTC. Further, the medical composition of the invention may also be evaluated by examining tumor size or survival rate in vivo, such as in an animal.

The life-lengthening effect of the medical composition of the invention can be evaluated by the % ILS (increase of life-span) calculated according to the following formula: [(mean survival days of treated group)−(mean survival days of control group)/(mean survival days of control group)]×100 (%). For example, when physiological saline is used as the control, the % ILS may be 100 or greater, preferably 120 or greater, more preferably 150 or greater, even more preferably 180 or greater and yet more preferably 200 or greater.

The present inventors have shown that using a composition of the invention can suppress tumor size increase and extend animal life, and completely cure MTC, in vivo, even after drug administration has been terminated. Treatment of MTC has conventionally been performed by surgical excision. The efficacy of irinotecan for MTC has previously been suggested, but the side-effects are serious, and no effective drug therapy has been established. The present invention is the first to disclose a medical composition that is effective for treatment, palliative care and prevention of cancer such as MTC. The present inventors have also found that non-drug-encapsulating liposomes containing Oct and PEG exhibit cytotoxicity for MTC cells. Oct has conventionally been used as a somatostatin receptor-detecting diagnostic agent, or as a ligand for targeted delivery of drugs, but non-drug-encapsulating Oct-modified liposomes themselves unexpectedly exhibited cytotoxicity. The in vivo effect on MTC exhibited by the medical composition of the invention may possibly be additive or synergistic reinforcement of the effect of encapsulated CPT-11 by Oct-modified liposomes. In an in vivo tumor bearing animal model experiment using medullary thyroid carcinoma (C cells), a CPT-11-encapsulating Oct-modified nanomedicine produced complete remission, in contrast to partial remission by the free drug and a non-ligand CPT-11-encapsulating nanomedicine. Since this is attributed to an augmenting effect by optimal modification with Oct, the Oct-modified nanomedicine of the invention is expected to have the same effect for other anticancer agents as well.

The present invention will now be explained in detail through the following examples, with the understanding that these examples are in no way limitative on the invention.

EXAMPLES

Example 1

Characterization of Oct-Modified Liposomes (1) Preparation and Modification of Liposomes Distearoylphosphatidylcholine (DSPC, NOF Corp.) and cholesterol (Chol, Wako Pure Chemical Industries, Ltd.) (molar ratio=55:45, weight ratio=80 mg:32 mg) were dissolved in ethanol, and a rotary evaporator set to 70° C. was used for removal of all but a trace amount of the ethanol. An 80 mM phytic acid (IP-6) solution (Nacalai Tesque, Inc.) adjusted to pH 6.5 with triethanolamine was added thereto, and the obtained mixture was vigorously shaken for 5 minutes while heating at 70° C., to obtain liposomes. The obtained liposomes were again processed with an evaporator to remove the remaining ethanol. The ultrasonically treated liposome sizes were approximately 150 nm. The external solution was exchanged with HBS buffer (20 mM HEPES, 150 mM NaCl, pH 7.4) by gel filtration using Sephadex G50, and the liposome fraction was collected. Wako Phospholipid Test (Wako Pure Chemical Industries, Ltd.) was used to measure the DSPC concentration of the collected liposome fraction. The total lipid content was calculated based on the determined DSPC concentration and the DSPC:Chol molar ratio (55:45).

An irinotecan ("CPT-11", Yakult Honsha Co., Ltd.) water-soluble solution (10 mg/ml) was added to the prepared liposome solution to CPT-11:total lipid=0.6:1 (weight ratio), and the mixture was incubated at 60° C. for 60 minutes, to encapsulate the CPT-11. For doxorubicin ("DXR", Wako Pure Chemical Industries, Ltd.)-encapsulating liposomes, DXR was added to DXR:total lipid=0.2:1 (weight ratio), and the mixture was incubated at 60° C. for 25 minutes to accomplish encapsulation. After incubation was complete, cooling was carried out on ice for 5 minutes to suspend the reaction. The non-encapsulated drug was removed by gel filtration using Sephadex G50, to obtain unmodified liposomes ("CL").

An aqueous solution of octreotide-poly(ethylene glycol)$_{3400}$-distearoylphosphatidylethanolamine (Oct-PEG-DSPE, KNC Laboratories Co., Ltd.) was added to the previously obtained CL to 0.25, 0.8, 1.0, 1.2, 1.4 or 1.6 mol % of total liposomal lipid, and the obtained mixture was heated at 60° C. for 20 minutes (modification after preparation), to obtain "0.25Oct-CL", "0.8Oct-CL", "1.0Oct-CL", "1.2Oct-CL", "1.4Oct-CL" and "1.6Oct-CL" as Oct-modified liposomes (Oct-CL).

(Method of Preparing 4.4Oct-CL)

For 4.4Oct-CL, the procedure was carried out using DSPC, Chol and Oct-PEG-DSPE (molar ratio=55:45:8.8; weight ratio=5.68 mg:2.28 mg:6 mg), accomplished by the same methods as for CL (modification before preparation).

PEGylated non-Oct-modified liposomes ("SL") were prepared by adding methoxy-poly(ethylene glycol)$_{2000}$-distearoylphosphatidylethanolamine (PEG-DSPE, NOF Corp.) at 1.6 mol % instead of Oct-PEG-DSPE.

Non-drug-encapsulating liposomes were prepared by the same procedure as the above-identified drug-encapsulating liposomes, except that no drug (CPT-11, DXR) was encapsulated.

(2) Characterization of Oct-Modified Liposomes

The size (nm) and zeta potential (mV) (using an ELS-Z2 by Otsuka Electronics Co., Ltd.), and the CPT-11-encapsulating rate (%) were measured for the obtained Oct-modified liposomes (0.25Oct-CL, 0.8Oct-CL and 1.6Oct-CL) and unmodified liposomes (CL) and PEGylated non-Oct-modified liposomes (SL). The drug concentration in the liposomes was measured using an UV-1700 PharmaSpec (Shimadzu Corp.) at 480 nm for DXR and using a Wallac ARVO SX1420 Multilabel counter (PerkinElmer) at an excitation wavelength of 375 nm and a fluorescent wavelength of 535 nm for CPT-11, after disruption of the liposomes with 1% Triton. The results are shown in Table 1 as mean±SD (n=3).

TABLE 1

| Formulation | Size (nm) | Zeta potential (mv) | CPT-11-encapsulating efficiency (%) |
|---|---|---|---|
| CL | 151.9 ± 5.5 | −5.1 ± 0.1 | 75.6 ± 1.9 |
| 0.25Oct-CL | 141.3 ± 6.1 | −11.2 ± 3.5 | 82.5 ± 2.7 |
| 0.8Oct-CL | 141.6 ± 9.4 | −17.8 ± 6.9 | 84.0 ± 7.4 |
| 1.0Oct-CL | 153.9 ± 6.2 | −18.1 ± 4.3 | — |
| 1.2Oct-CL | 134.2 ± 5.4 | −15.3 ± 1.9 | — |
| 1.4Oct-CL | 147.6 ± 2.4 | −17.3 ± 4.7 | — |
| 1.6Oct-CL | 136.6 ± 3.2 | −19.5 ± 1.3 | 87.2 ± 2.9 |
| SL | 144.7 ± 1.6 | −20.1 ± 1.6 | 81.9 ± 4.5 |

The zeta potential of the liposomes decreased with increasing octreotide (Oct) concentration (0 to 1.6 mol %). This suggests that the liposomes had been modified with Oct. The final Oct concentration after modification of the liposomes was measured using an Oct-EIA kit (Peninsula Laboratories) after 1:1000 dilution with 1% Triton, and the amount of Oct of the Oct-modified liposomes were all greater than 70% of the theoretical value. The CPT-11-encapsulating efficiency was >82% for all of the liposomes other than CL. The mean diameters of all of the liposome types and the encapsulated CPT-11 concentrations were unchanged during at least 1 month at 4° C. in dark surroundings.

Example 2

Effect of Oct Concentration on Intracellular Uptake

TT cells (obtained from European Collection of Cell Cultures (ECACC)), a human medullary thyroid carcinoma cell line that highly expresses somatostatin receptor (SSTR), were seeded in Ham's F-12 culture medium supplemented with 10% heat-inactivated fetal bovine serum (FBS) in a 6-well plate at a density of $10^4$ cells/well, and cultured for 72 hours. To the cells there was added medium (2 ml/well) containing 0.25Oct-CL, 0.8Oct-CL, 1.0Oct-CL, 1.2Oct-CL, 1.4Oct-CL, 1.6Oct-CL, 4.4Oct-CL or SL at 50 µg/ml as the DXR concentration, and incubation was performed at 37° C. for 1 or 2 hours. Since CPT-11 is not excited by the wavelengths listed below, liposomes encapsulating DXR instead of CPT-11 were used for this example. The medium was removed and rinsing was performed 3 times with PBS (pH 7.4), after which intracellular uptake of the liposomes was analyzed using a FACS Calibur flow cytometer (Becton-Dickinson) equipped with a 488 nm argon ion laser, and CELL Quest software (Becton-Dickinson Immunocytometry System). The relative mean fluorescence intensities after 2 hours of culturing are shown in FIG. 1. In FIG. 1, 0.25, 0.8, 1.0, 1.2, 1.4, 1.6, 4.4 and SL represent the results for 0.25Oct-CL, 0.8Oct-CL, 1.0Oct-CL, 1.2Oct-CL, 1.4Oct-CL, 1.6Oct-CL, 4.4Oct-CL and SL, respectively, and the "*" symbol indicates a statistically significant difference from SL ($p<0.05$).

As shown in FIG. 1, intracellular uptake of 0.25Oct-CL and 0.8Oct-CL was rather lower than SL that was not modified with Oct. Also, no significant difference was found between 0.25Oct-CL and 0.8Oct-CL. On the other hand, intracellular uptake of 1.4Oct-CL, 1.6Oct-CL and 4.4Oct-CL was significantly higher than the others. That is, no augmenting effect on intracellular uptake is observed with Oct modification at a low Oct concentration such as used in the prior art (about 0.5%), whereas Oct modification at a high Oct concentration (1.6 mol %) is effective for exhibiting cytotoxicity.

The fluorescence intensity of 1.6Oct-CL after 2 hours of incubation increased 2-fold of after 1 hour incubation, but no such increase was observed with SL. In other words, intraellular uptake Oct-CL was shown to increase in a manner dependent on incubation time.

Example 3

Competitive Inhibition Test

A competitive inhibition test was conducted to examine whether or not the intracellular uptake observed in Example 2 takes place via somatostatin receptor (SSTR). Specifically, TT cell uptake of DXR-encapsulating 1.6Oct-CL (Oct:4.2 nmol/ml) in the presence of free Oct (Acris Antibodies GmbH) in a 20-fold molar excess (84 nmol/ml) at 37° C. for 2 hours was examined by flow cytometry. As a result, the excess of free Oct did not affect intracellular uptake of 1.6Oct-CL. The reason for this is not fully understood, but the results mentioned above suggest that the affinity of Oct-modified liposomes for SSTR is higher than free Oct.

Figure 2:
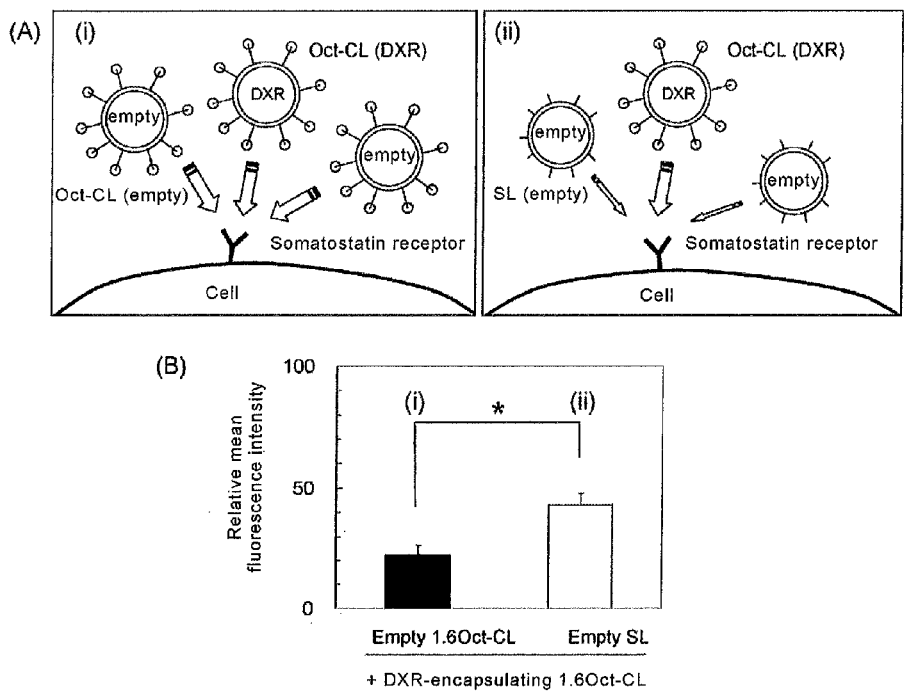
FIG. 2 provides the results of a competitive inhibition test.
Figure 3:
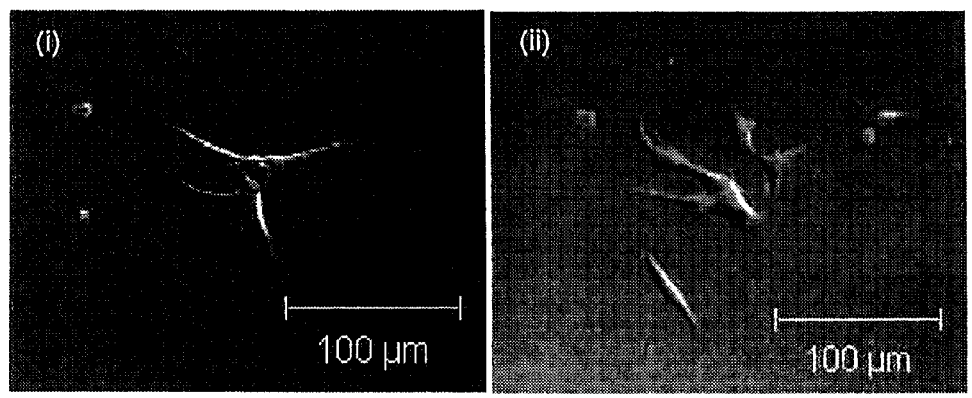
FIG. 3 provides the results of a competitive inhibition test.

Next, TT cell uptake of DXR-encapsulating 1.6Oct-CL at 37° C. for 2 hours, in the presence of a 2-fold volume (258 µL) of non-drug-encapsulating empty 1.6Oct-CL (Empty 1.6Oct-CL), or Empty SL as a control was examined by flow cytometry. The results showed inhibition in all cases, but the intracellular uptake in the presence of Empty Oct-CL was about half that in the presence of Empty SL, indicating highly significant competitive inhibition of intracellular uptake by Empty Oct-CL (FIG. 2(B)). The competitive inhibition is shown schematically in FIG. 2(A). In addition, confocal microscope observation revealed that the encapsulated drug (DXR) had been taken up into the nuclei (FIG. 3). Thus, uptake of drug-encapsulating 1.6Oct-CL into the nuclei was shown to be dependent on Oct modification.

Example 3

Cytotoxicity Test (1) Cytotoxicity Test Using CPT-11-Encapsulating Liposomes

TT cells were seeded into a 96-well plate at a density of $10^4$ cells/well, and free CPT-11, 1.6Oct-CL or SL was added thereto at various concentrations prior to incubation for 48 hours, 72 hours and 96 hours. Next, after rinsing the cells with PBS, a coloring reagent (Cell Counting kit-8, Dojindo Laboratories) was added at 10 µL per well (100 µL), the absorbance at 450 nm was measured and IC50 (µM) was calculated. The results are shown in Table 2.

TABLE 2

| | IC50 (µM) | | |
| --- | --- | --- | --- |
| Formulation | 48 hrs | 72 hrs | 96 hrs |
| Free CPT-11 | 13.4 | 6.6 | 2.2 |
| 1.6Oct-CL | 35.7 | 8.7 | 1.4 |
| SL | 34.4 | 8.0 | 2.3 |

As shown in Table 2, the cytotoxicity increased with time in all cases. The IC50 value for SL at 96 hours was approximately the same as for free CPT-11. On the other hand, the cytotoxicity of 1.6Oct-CL was lower than free CPT-11 at 48 hours, while at 96 hours it had increased over that of free CPT-11 by about ½ of free CPT-11. That is, while cytotoxicity was observed with all of the drug-encapsulating liposomes, the cytotoxicity was enhanced after prolonged incubation when using Oct-modified drug-encapsulating liposomes. It was also confirmed that this is due to accelerated intracellular uptake by a receptor-mediated endocytosis mechanism, enhancing the CPT-11 cytotoxicity exhibited by conversion to the active form of SN-38 (data not shown).

(2) Cytotoxicity Test Using Non-Drug-Encapsulating Liposomes

The results described above suggested the possibility that Oct-modified liposomes themselves, as ligands for targeting, have cytotoxicity in addition to CPT-11. Next, a cytotoxicity test was conducted using non-CPT-11-encapsulating liposomes, in order to evaluate the effect of the ligand (Oct) on cytotoxicity. Specifically, to TT cells seeded in a 96-well plate there were added PEGylated non-Oct-modified liposomes (Empty SL), without the encapsulation of different concentrations of drug (0.042-8.4 µM Oct), non-drug-encapsulating 1.6 mol % Oct-modified liposomes (Empty 1.6Oct-CL), non-drug-encapsulating 4.4 mol % Oct-modified liposomes (Empty 4.4Oct-CL) and free Oct as a control, and incubation was performed for 96 hours. After rinsing the cells with PBS, a coloring reagent was added and the absorbance at 450 nm was measured. The Empty 4.4Oct-CL was prepared in the same manner as Example 1, except that initially Oct-PEG-DSPE was added to DSPE:Chol:Oct-PEG-DSPE=55:45:8.8 (molar ratio). This is because modification after preparation is difficult with a concentration higher than 1.6 mol %, due to the low water solubility of Oct-PEG-DSPE.

Figure 4:
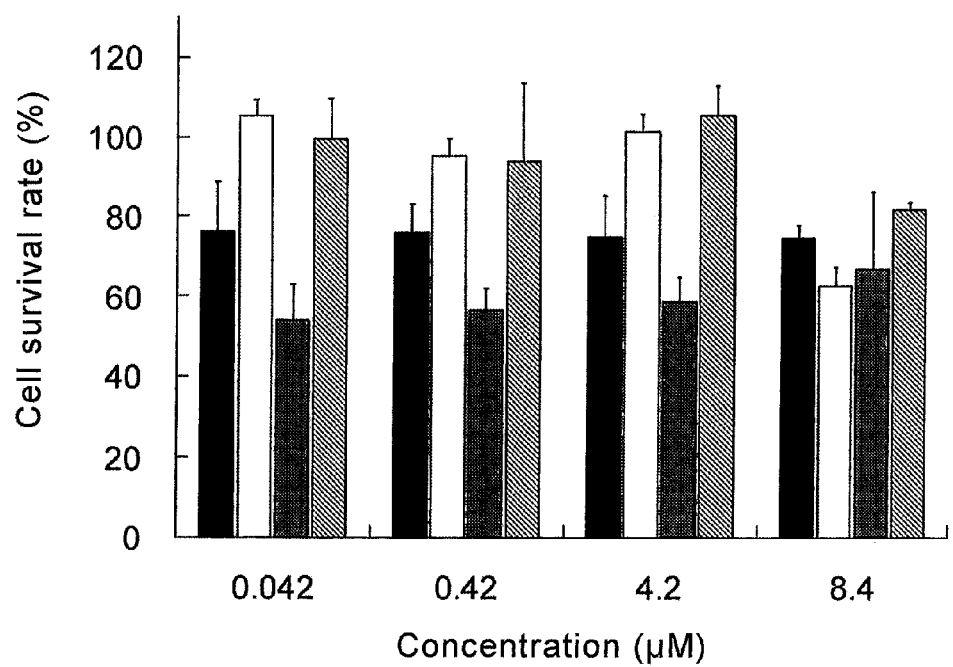
FIG. 4 provides the results of a cytotoxicity test using non-drug-encapsulating liposomes.

The results are shown in FIG. 4. In FIG. 4, the four bars for each concentration are, from the left, the cell survival rates (%) for free Oct, Empty 1.6Oct-CL, Empty 4.4Oct-CL and Empty SL, respectively. Cytotoxicity was observed for free Oct at all concentrations. In the liposomes, Empty 4.4Oct-CL modified with a high concentration of Oct exhibited particularly high cytotoxicity at all concentrations, and this was higher than free Oct. This result suggests that high concentration Oct in liposomes exhibits cytotoxicity.

(3) Effect of Oct-CL on phosphorylation of Akt, TSC2 and p70S6K

Figure 5:
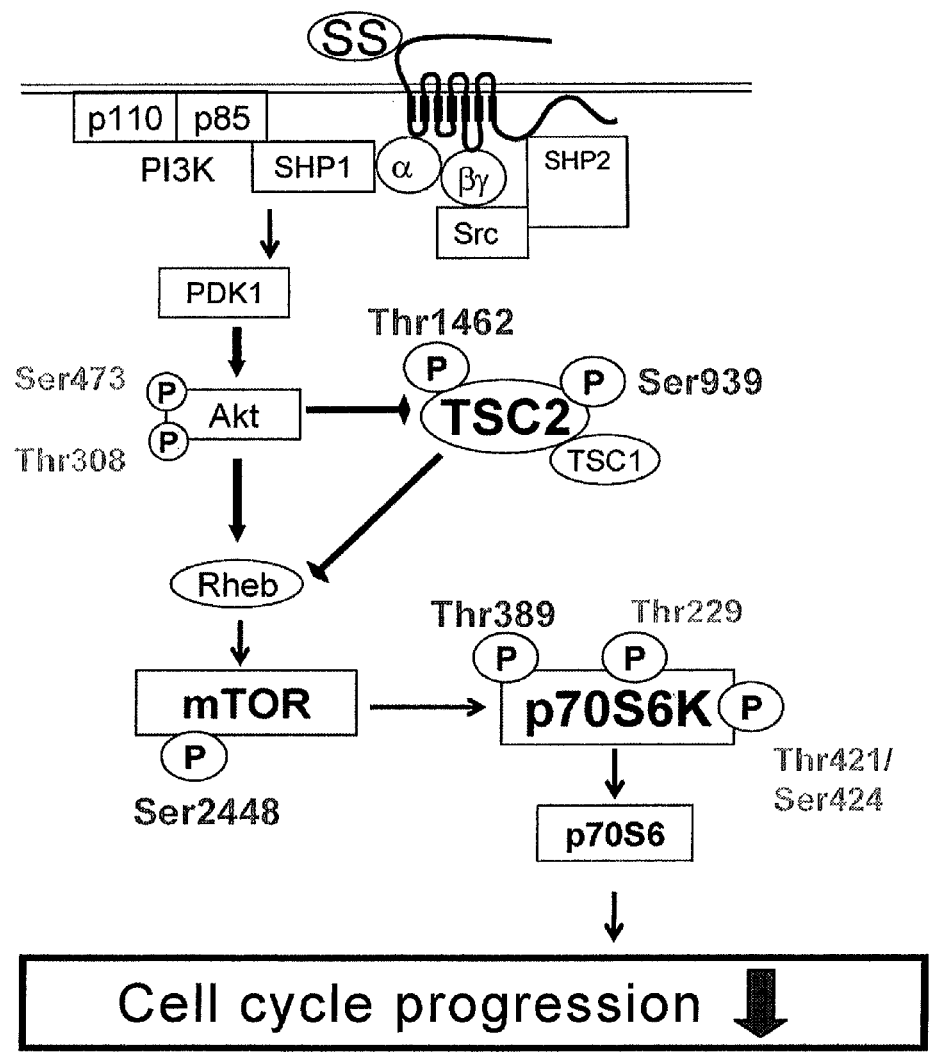
FIG. 5 provides the PI3K/Akt/TSC2/mTOR/p70S6K signal cascade.

Oct is known to contribute to phosphorylation of TSC2, mTOR and p70S6K proteins in the PI3K/Akt/TSC2/mTOR/p70S6K signal cascade (FIG. 5). In order to investigate the relationship between cytotoxicity of Oct and the PI3K/Akt/TSC2/mTOR/p70S6K signal cascade, the effect of Empty 1.6Oct-CL on phosphorylation of Akt, TSC2 and p70S6K in this pathway was examined. Specifically, TT cells were treated for 24 hours with Empty 1.6Oct-CL (0.42 µM as Oct concentration) or Empty SL (amount corresponding to the lipid in Empty 1.6Oct-CL), after which Akt (molecular weight: 60 kDa), TSC2 (molecular weight: 200 kDa) and p70S6K protein (molecular weights: 70 kDa, 85 kDa) in cell extract (protein: 40 µg/lane) were electrophoresed, and detection was performed using Akt-antibody, TSC2-antibody, p70S6K-antibody, phospho-Akt-antibody, phospho-TSC2-antibody and phospho-p70S6K-antibody (Cell Signaling Technology, all 1000-fold dilutions) as primary antibody and goat anti-rabbit-HRP (Santa Cruz Biotechnology, 2500-fold dilution) as secondary antibody.

Figure 6:
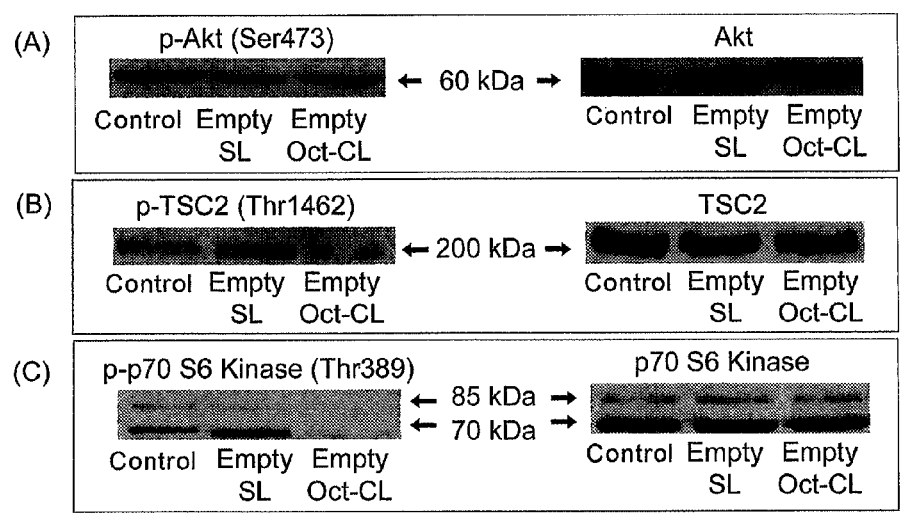
FIG. 6 provides the effects of Oct-CL on phosphorylation of Akt, TSC2 and p70S6K.

As shown in FIG. 6, addition of Empty 1.6Oct-CL reduced phosphorylation of p70S6K, but did not affect phosphorylation of Akt or TSC2. Empty SL did not affect phosphorylation of Akt, TSC2 or p70S6K which were examined in this test. This suggests that the cytotoxicity of Empty Oct-CL is related to reduced phosphorylation in the PI3K/Akt/TSC2/mTOR/p70S6K signal cascade. In addition, since the reduced phosphorylation did not occur with Empty SL, this suggests that it is related to the ligand Oct, instead of being an effect of the lipids composing the liposomes.

Example 4

Effect of CPT-11-Encapsulating Liposomes In Vivo

Figure 7:
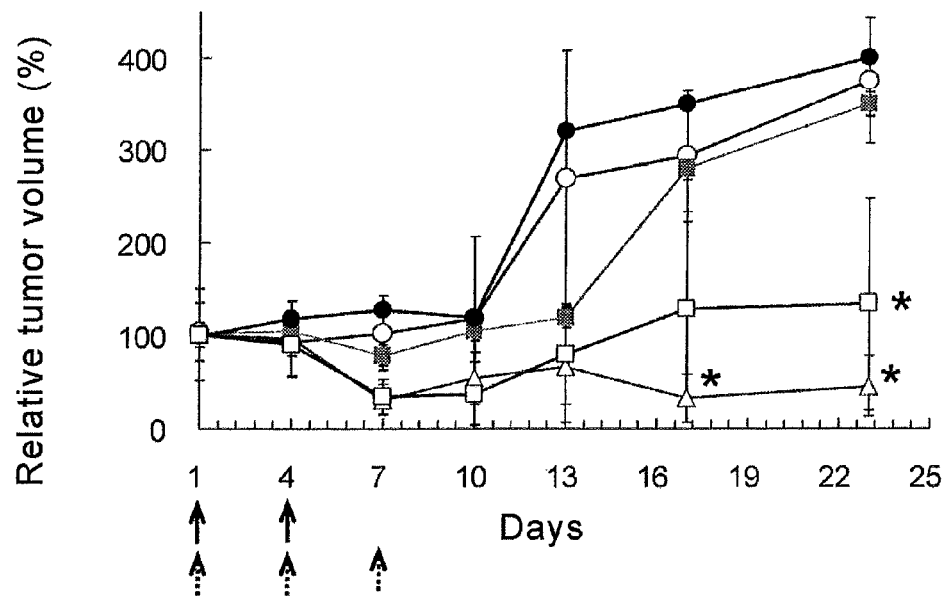
FIG. 7 provides the effect of CPT-11-encapsulating liposomes on tumor size.
Figure 8:
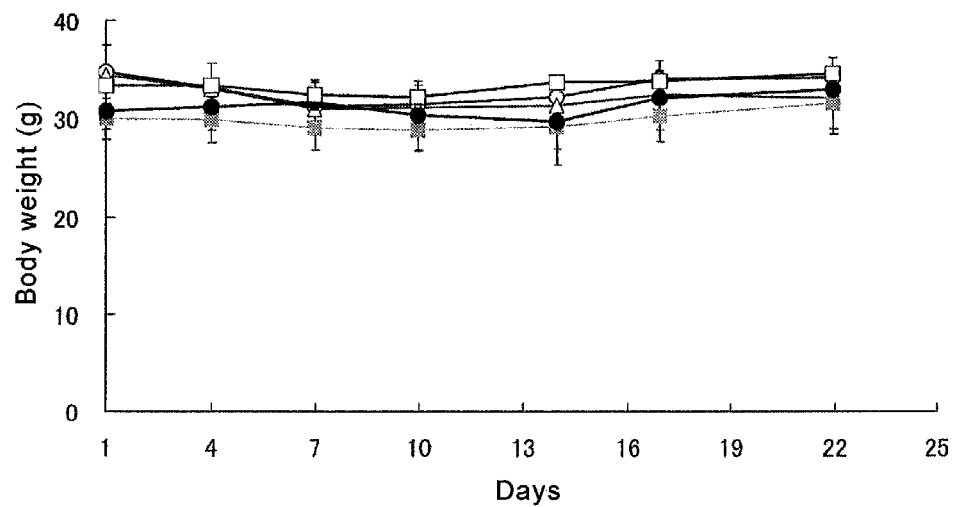
FIG. 8 provides the effect of CPT-11-encapsulating liposomes on body weight.
Figure 9:
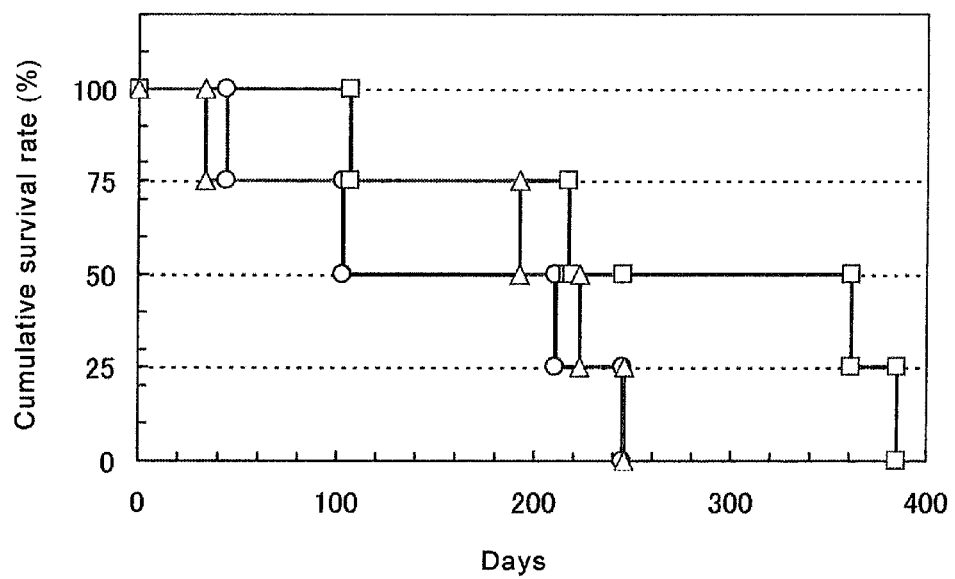
FIG. 9 provides the effect of CPT-11-encapsulating liposomes on survival rate.

The following test was conducted to examine the in vivo effect of CPT-11-encapsulating Oct-modified liposomes. After transplanting $10^7$ TT cells into mice (ICR nu/nu mice, 6-week-old, female, Oriental Yeast Co., Ltd.), tumors with tumor volumes of 100 to 250 cm³ formed. To four mice in each group there were administered unmodified liposomes (CL) at 10 mg/kg body weight, as the CPT-11 amount, liposomes modified with 1.6 mol % Oct-PEG-DSPE (1.6Oct-CL), and liposomes modified with 1.6 mol % Oct-PEG-DSPE and 0.9% mol % PEG-DSPE (1.6Oct-SL). The administration was twice (1st and 4th days) through the caudal vein. As a control there was administered physiological saline and free CPT-11 (30 mg/kg), three times (1st, 4th and 7th days). The tumor size and body weight were periodically measured. The results are shown in FIGS. 7 and 8. In FIGS. 7 and 8, the white circles, triangles, grey squares, black circles and white squares represent the results for CL, 1.6Oct-CL, free CPT-11, physiological saline and 1.6Oct-SL, respectively. In FIG. 7, the solid arrows indicate administration of CL, 1.6Oct-CL and 1.6Oct-SL, and the broken arrows indicate free CPY-11 and physiological saline, while "*" indicates significant difference with respect to CL (p<0.05). The survival times and cumulative survival rates are shown in Table 3 and FIG. 9. In FIG. 9, the circles, squares and triangles represent the results for CL, 1.6Oct-CL and 1.6Oct-SL, respectively. The column headed "% ILS" in Table 3 contains the values calculated by the formula: [(mean survival days of treated group)−(mean survival days of control group)/(mean survival days of control group)]×100(%), with physiological saline as the control. The column headed "Median" in Table 3 contains the median values for survival time (days) for each group consisting of N animals.

TABLE 3

| | Survival time | |
|---|---|---|
| | Median (N) | % ILS |
| Physiological saline | 67.5 (4) | — |
| Free CPT-11 | 88 (4) | 30.4 |
| CL | 103 (4) | 52.6 |
| 1.6Oct-CL | 217 (4) | 221.5 |
| 1.6Oct-SL | 192 (4) | 184.4 |

No significant difference in body weight was observed during the measurement period. When free CPT-11 was administered, tumor size increased and no life-lengthening effect was observed, similar to when physiological saline was administered. Essentially the same results were seen for CL as well. On the other hand, administration of Oct-modified liposomes (1.6Oct-CL, 1.6Oct-SL) significantly suppressed tumor size increase and significantly increased survival time and survival rate in both cases. Particularly in the 1.6Oct-CL treated group, half of the animals survived for at least 300 days even after suspending drug administration, suggesting total cure of the tumor.

Free CPT-11 exhibited cytotoxicity in vitro (Example 3, Table 2, FIG. 4), in vivo, it only exhibited the same effect as physiological saline which was used as the control. It was therefore difficult to predict an in vivo effect based on in vitro results. The present inventors have been the first to demonstrate that MTC, for which no effective drug therapy has been established to date, can be cured in vivo using Oct-modified liposomes. Also, the dosage of CPT-11 when using Oct-modified liposomes was significantly lower than the free CPT-11 dosage (⅓). In other words, it was shown that the invention allows CPT-11 dosage to be reduced and side-effects to be alleviated.

Figure 10:
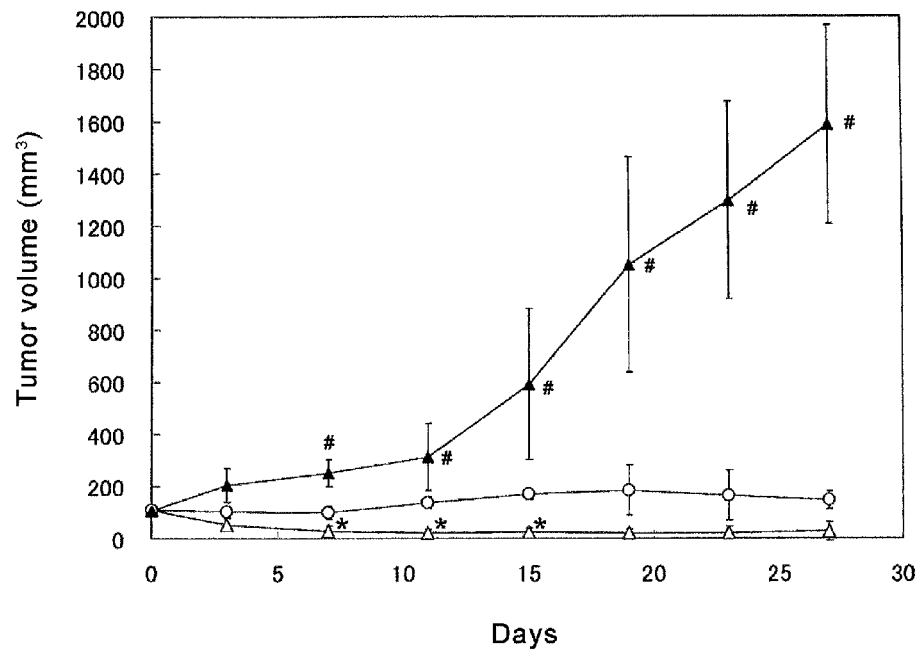
FIG. 10 provides the effect of CPT-11-encapsulating liposomes on tumor size.
Figure 11:
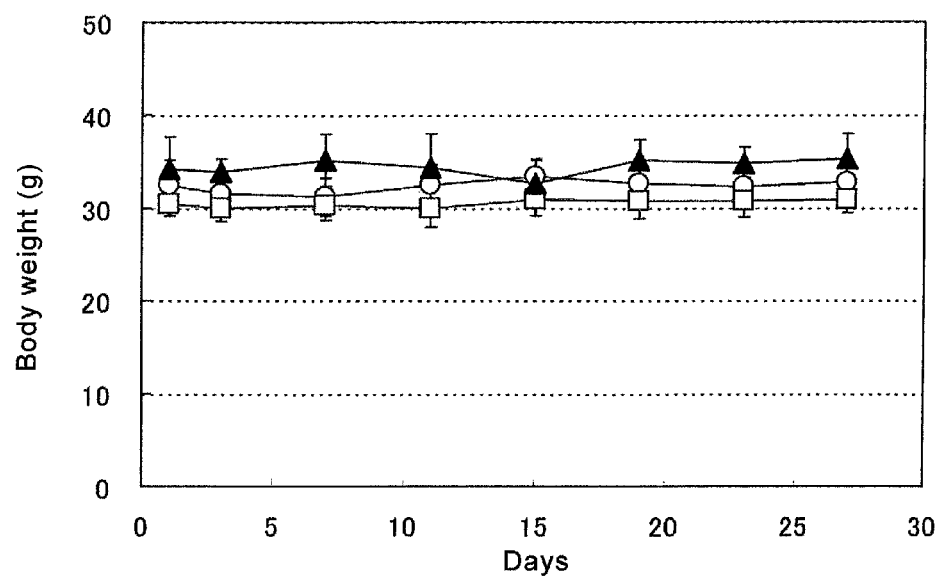
FIG. 11 provides the effect of CPT-11-encapsulating liposomes on body weight.
Figure 12:
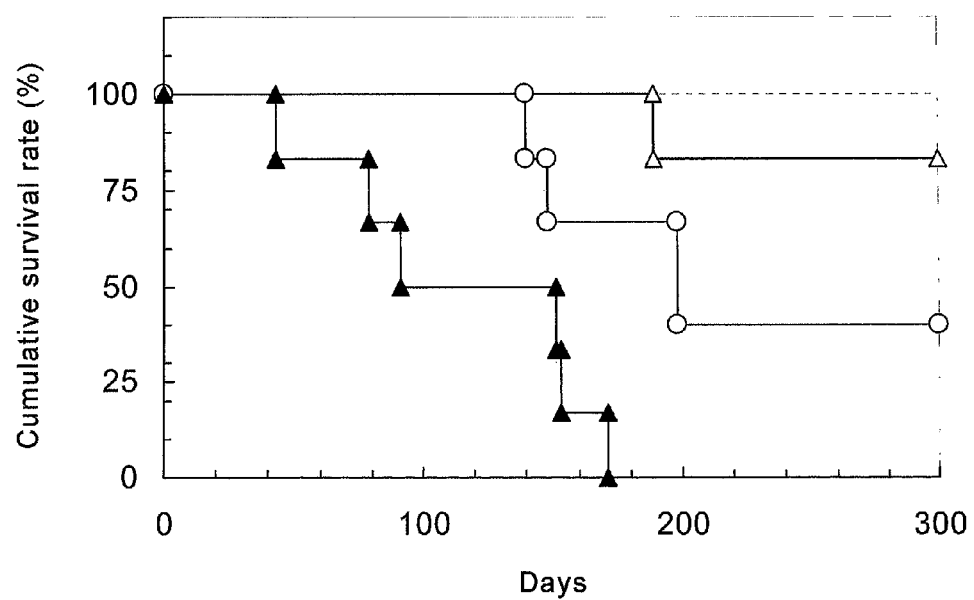
FIG. 12 provides the effect of CPT-11-encapsulating liposomes on survival rate.

In the same manner, liposomes modified with 1.6Oct-CL and 2.5% mol % PEG-DSPE (2.5Oct-SL) at 10 mg/kg body weight as the amount of CPT-11, and physiological saline as a control, were administered twice (1st and 4th days) through the caudal vein to six mice in each group having tumors with tumor volumes of 100 cm³, and the tumor sizes, body weights and survival rates were periodically measured. The results are shown in FIGS. 10, 11 and 12. In FIGS. 10, 11 and 12, the white triangles, circles and black triangles represent the results for 1.6Oct-CL, SL and physiological saline, respectively. In FIG. 10, the "*" and "#" symbols indicate significant difference with respect to SL and 1.6Oct-CL (p<0.05). In this case as well, tumor size increase was almost completely suppressed in the 1.6Oct-CL administered group, even after drug administration was suspended. Tumor size suppression was also seen with non-Oct-modified SL, but the suppressing effect was significantly higher in the 1.6Oct-CL administered group.

INDUSTRIAL APPLICABILITY

According to the invention there is provided a medical composition for treatment, palliative care or prevention of cancer such as medullary thyroid carcinoma, which comprises liposomes modified with octreotide.

The invention claimed is:

1. A medical composition for treatment, palliative care or prevention of cancer, which comprises liposomes modified with octreotide after preparation of the liposomes, wherein the concentration of octreotide in the liposomes is 1.4 mol % or more, wherein the liposomes are taken up by a cell dependent on octreotide modification, and wherein the liposomes are prepared by phospholipids solely selected from the group consisting of phosphatidylethanolamine, phosphatidylinositol, sphingomyelin, disteroylphosphatidylcholine (DSPC) and distearoylphosphatidylethanolamine (DSPE) and mixtures thereof.

2. The medical composition according to claim 1, wherein the % ILS representing the Increase of Life-Span, with physiological saline as the control, is 100 or greater.

3. The medical composition according to claim 1, wherein irinotecan is encapsulated in the liposomes.

4. The medical composition according to claim 3, wherein the irinotecan dosage is no greater than 20 mg/kg body weight.

5. The medical composition according to claim 1, wherein the cancer is medullary thyroid carcinoma.

* * * * *